(12) United States Patent
Toumazou et al.

(10) Patent No.: US 12,024,739 B1
(45) Date of Patent: Jul. 2, 2024

(54) METHOD AND APPARATUS FOR RAPID ANALYSIS OF A BIOLOGICAL SAMPLE

(71) Applicant: DnaNudge Limited, London (GB)

(72) Inventors: Christofer Toumazou, London (GB); Rashmita Sahoo, London (GB)

(73) Assignee: DnaNudge Limited, London (GB)

(*) Notice: Subject to any disclaimer, the term of this patent is extended or adjusted under 35 U.S.C. 154(b) by 0 days.

(21) Appl. No.: 18/184,615

(22) Filed: Mar. 15, 2023

(51) Int. Cl.
 *C12Q 1/6827* (2018.01)
 *C12Q 1/6844* (2018.01)

(52) U.S. Cl.
 CPC ......... *C12Q 1/6827* (2013.01); *C12Q 1/6844* (2013.01)

(58) Field of Classification Search
 CPC .............................. C12Q 1/6827; C12Q 1/6844
 See application file for complete search history.

(56) References Cited

U.S. PATENT DOCUMENTS

| 2015/0353919 | A1* | 12/2015 | Mielke | B01L 3/5029 |
| | | | | 435/6.12 |
| 2018/0087097 | A1* | 3/2018 | Toumazou | C12Q 1/6827 |

FOREIGN PATENT DOCUMENTS

| WO | WO-2014138396 A1 * | 9/2014 | ........... C12Q 1/6886 |
| WO | 2018055407 A1 | 3/2018 | |
| WO | WO-2019118550 A1 * | 6/2019 | ......... C12N 15/1003 |

OTHER PUBLICATIONS

Burdett et al. BMC Infectious Diseases. 2021. 21:665. (Year: 2021).*
DNAgenotek. "Inactivation of SARS-CoV-2 in samples using Oragene, ORAcollect and OMNIgene products from DNAgenote" 2020. (Year: 2020).*
ORG-500 Data Sheet. Jan. 2012. (Year: 2012).*
Gibani et al. Lancet Microbe. 2020. 1:e300-07. (Year: 2020).*
Piret et al. Current Drug Targets. 2002. 3:17-30. (Year: 2002).*
Howett et al. Antimicrobial Agents and Chemotherapy. 1999. 43(2):314-321. (Year: 1999).*

* cited by examiner

*Primary Examiner* — Joseph G. Dauner
(74) *Attorney, Agent, or Firm* — Michael Best & Friedrich LLP

(57) ABSTRACT

A method of analysing a sample comprising nucleic acid. The method includes introducing the sample into a discrete container that is prefilled with a lysis buffer. Agitating the container to assist with lysing to release nucleic acid. Extracting a lysed sample from the container and introducing the lysed sample into a sample chamber of a disposable cartridge. Mixing the lysed sample with a dilution buffer in the sample chamber to obtain a first mixture. Fluidly connecting the sample chamber to a mixing chamber. "Displacing the first mixture from the sample chamber to the mixing chamber. Fluidly connecting the mixing chamber to a mastermix chamber containing a mastermix. Displacing the first mixture to obtain a second mixture." Displacing the second mixture from the mastermix chamber to an analysis unit. Operating the analysis unit to identify the nucleic acid or other nucleic acids derived from the nucleic acid.

11 Claims, 10 Drawing Sheets

METHOD AND APPARATUS FOR RAPID ANALYSIS OF A BIOLOGICAL SAMPLE

TECHNICAL FIELD

The present invention relates to a method and apparatus for processing a biological sample to perform nucleic acid detection and genotyping, such as Single Nucleotide Polymorphism (SNP) genotyping, on a sample of genetic material. The present invention further relates to a method and apparatus for analysing a biological sample for performing diagnostic testing on a sample of genetic material.

BACKGROUND

Compact sequencing devices allow genetic material to be detected outside of a lab environment. These devices enable real time detection of DNA and RNA using a streamlined workflow without the need for additional, specialized equipment or technicians.

One example of such a system is disclosed in WO2018055407, the entire contents of which are hereby incorporated by reference in its entirety. The system is suitable for the detection of DNA (or RNA) in a sample of biological material. The system comprises a test cartridge and a base unit for controlling the operation of the test cartridge. The test cartridge contains reagents in chambers for preparing a sample for amplification. Once a sample is inserted in the test cartridge, the reagents are mixed with the sample by transferring the reagents between the chambers. All of the sample preparation steps, including lysing, washing and elution, take place within the cartridge itself. Following this, the sample is transferred to an amplification unit within the test cartridge to detect DNA in real time by e.g., PCR (polymerase chain reaction).

PCR reactions work by amplifying a target strand of DNA in a sample over a series a cycles. The amplified strands of DNA contain fluorescent reporter dyes so that the presence of the target strand can be confirmed. PCR reactions must be performed using alternating temperature steps. Other DNA amplification techniques are available such as LAMP (loop-mediated isothermal amplification), which carries out amplification over a constant temperature. Since LAMP amplifies a target strand with high specificity and without the need for expensive reagents or instruments, it is especially useful for diagnostic testing.

The coronavirus pandemic has highlighted the need for rapid diagnostic testing in both the home and clinical settings. In order to detect viral RNA, RT-PCR (reverse transcriptase-PCR) or RT-LAMP (reverse transcriptase-LAMP) amplification must be used. These techniques are similar to PCR and LAMP except that they first begin by performing reverse transcription of the RNA in order to obtain DNA. The procedure then continues by amplifying the DNA using the PCR or LAMP method.

While RT-PCR testing is considered to be the most sensitive type of test for COVID, the results of consumer tests are usually received days after the sample is taken. Due to the obvious need to reduce the spread of infection, it is preferable that results are received as soon as possible. It would also be desirable to rapidly diagnose the presence of other pathogens that can rapidly outbreak in a population, such as Strep-A.

As well as diagnostic testing to confirm to presence of a pathogen, it is also desirable that the results of genotyping are received as quickly as possible. Genotyping is the determination of variants in the genetic make-up of a subject. SNP genotyping is the measurement of genetic variations of single nucleotide polymorphisms (SNPs), which are mutations at a specific base pair mutation at a specific point of the genome. SNP genotyping can provide insights into predispositions an individual might have for certain diseases. Due to the life-changing impact that the results of such tests can have for an individual, it is desirable that results of such tests are received quickly.

SUMMARY

According to a first aspect of the present invention there is provided a method of analysing a sample comprising nucleic acid. The method comprises introducing said sample into a discrete container that is prefilled with a lysis buffer and agitating the container to assist with lysing to release nucleic acid. The lysed sample is then extracted from the container and introduced into a sample chamber of a disposable cartridge where it is mixed with a dilution buffer in the sample chamber to obtain a first mixture. The sample chamber is then fluidly connected to a mixing chamber, and the first mixture displaced from the sample chamber to the mixing chamber. The mixing chamber is fluidly connected to a mastermix chamber containing a mastermix, and the first mixture displaced from the mixing chamber to the mastermix chamber to obtain a second mixture. Thereafter, the second mixture is displaced from the mastermix chamber to the analysis unit, and the analysis unit operated to identify all, or parts of, the nucleic acid or other nucleic acid derived from the first mentioned nucleic acid.

It is preferable although not essential that the various steps be performed consecutively and without any intermediate steps, including elution, nucleic acid capture, and washing.

The sample may contain biological cells containing said nucleic acid.

The nucleic acid may be DNA or RNA.

The sample may be lysed in lysis buffer with a pH between 12 and 14.

The analysis unit may be configured and operated to identify all, or parts of, the nucleic acid or other nucleic acid using PCR or LAMP.

The step displacing the second mixture from the mastermix chamber to the analysis unit may comprise:
displacing the second mixture from the mastermix chamber back into the mixing chamber;
fluidly connecting the mixing chamber to an analysis unit; and
displacing the second mixture from the mixing chamber to the analysis unit.

The sample chamber and said mastermix chamber may be provided within an outer housing of a disposable cartridge and said mixing chamber is provided within an inner housing of the disposable cartridge, the inner and outer housings being rotatable relative to one another about a central axis in order to facilitate said steps of fluidly connecting.

Displacement of mixtures between the various chambers may be achieved by applying a positive or negative air pressure to the mixing chamber.

The steps may be performed in sequence and without any intervening elution and/or washing steps.

The step of agitating the container may comprise a manual agitation of the container.

DETAILED DESCRIPTION

A system and method for processing a biological sample to perform nucleic acid detection and, optionally, genetic testing or diagnostic testing will now be described. The system processes the sample in a relatively short time frame. Due to the speed with which the biological sample is processed, the system and method are particularly suitable for use in a non-medical environment such as the home or a retail premise, although medical uses are envisaged. The method and system aim to offer a relatively small physical footprint, be available at a relatively low cost, and be operable by a non-technical person such as a consumer or shop assistant.

Test Tube Analysis and Lysis Buffer

Figure 1:
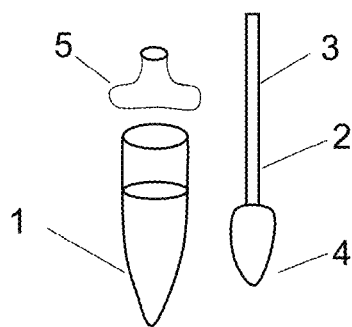
FIG. 1 shows a swab and tube for collecting a biological sample.

FIG. 1 shows a tube 1 for collection of a biological sample. This may be of a known type, for example similar to those tubes used to collect samples for a CIVID lateral flow test. Such tubes and the procedure for using them are now well known to the general public. The tube 1 is a reaction tube and is a suitable size for receiving the head of a swab 2. The swab 2 may be any type of swab suitable for obtaining a biological sample in order to perform diagnostics, such as an isohelix cheek swab, a nasopharyngeal swab or a baby swab. The swab 2 comprises a handle 3 connected to a tip 4 at one end of the handle 3. The tip 4 is located at the head of the swab 2 and is suitable for collecting secretion from a body part of a subject. The tip 4 may be made from nylon, viscose or cotton for example.

The tube 1 is flexible and can be made of a plastic such as polypropylene. The tube 1 further comprises a cap 5 for closing an open end of the tube 1. The cap 5 has an opening for expelling droplets from the tube 1. The cap 5 may be suitable for, but not limited to, expelling droplets with a size of 25 ul+/−5 ul.

The tube 1 is pre-filled with a high pH buffer solution for lysing cells. Preferably, the buffer solution has a pH of between 12 and 14. In one example, the buffer solution is NaOH 37.48 mM and EDTA 0.2 mM. The tube 1 may further comprise an aluminium oxide membrane covering the opening of the cap 5. Droplets expelled through the opening of the cap 5 will be filtered through the membrane and the purity of the genetic material in the droplets can thereby be increased.

Cartridge

Figure 2:
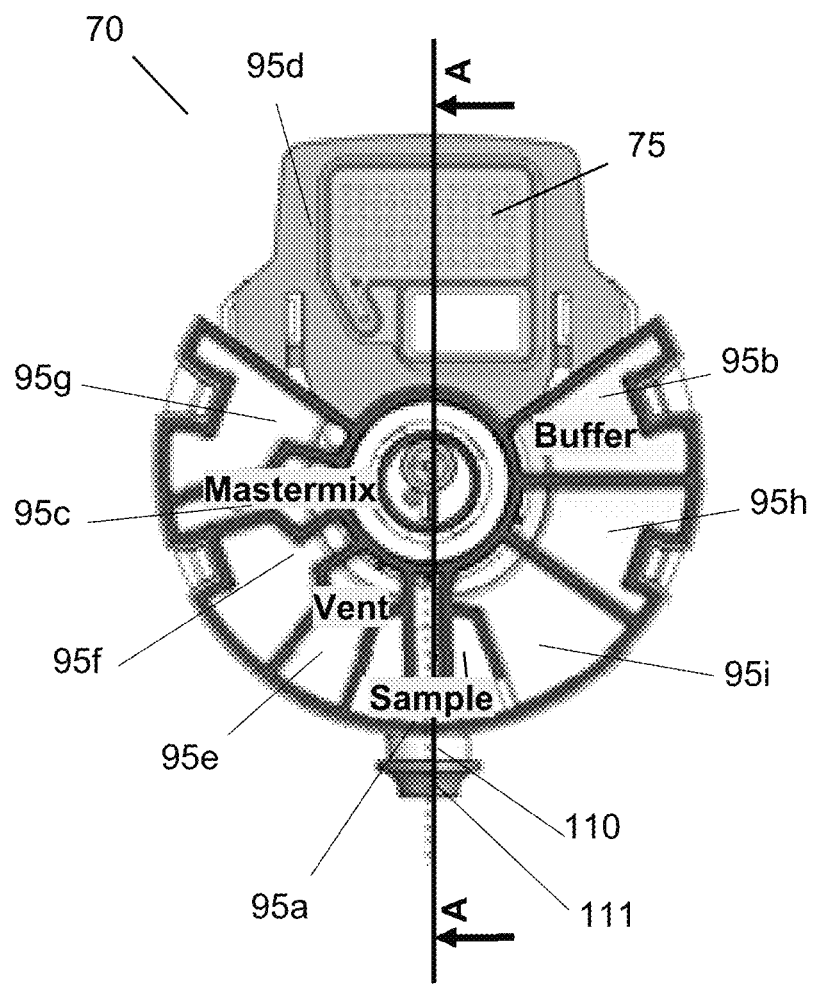
FIG. 2 shows a test cartridge for performing analysis of a biological sample.

FIG. 2 shows a test cartridge 70 for receiving a biological sample, processing it, and analysing it. The test cartridge 70 docks with a base unit 65 or instrument as will be described further below. Whilst the base unit 65 is intended to be reusable many times, the test cartridge 70 is intended to be single use and disposable. The test cartridge 70 is configured to be clipped into the base unit 65.

The test cartridge 70 comprises a multi-chamber unit 75 comprising a plurality of chambers 95*a-i* divided by radially extending walls. Each of the chambers is suitable for containing a sample and or reagents. In the example shown, chamber 95*a* receives a biological sample, chamber 95*b* contains a dilution buffer and chamber 95*c* comprises mastermix. An analysis unit 71 is installed in the analysis chamber 95*d*. In the present example, the analysis chamber 95*b* provides a vacant slot for receiving the analysis unit 71. The chambers are described in further detail below.

Figure 3:
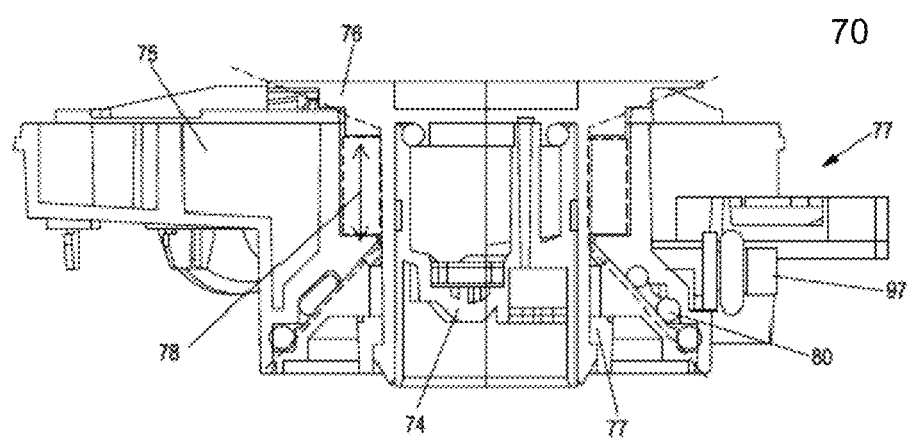
FIG. 3 shows a side view of the test cartridge of FIG. 2.
Figure 4:
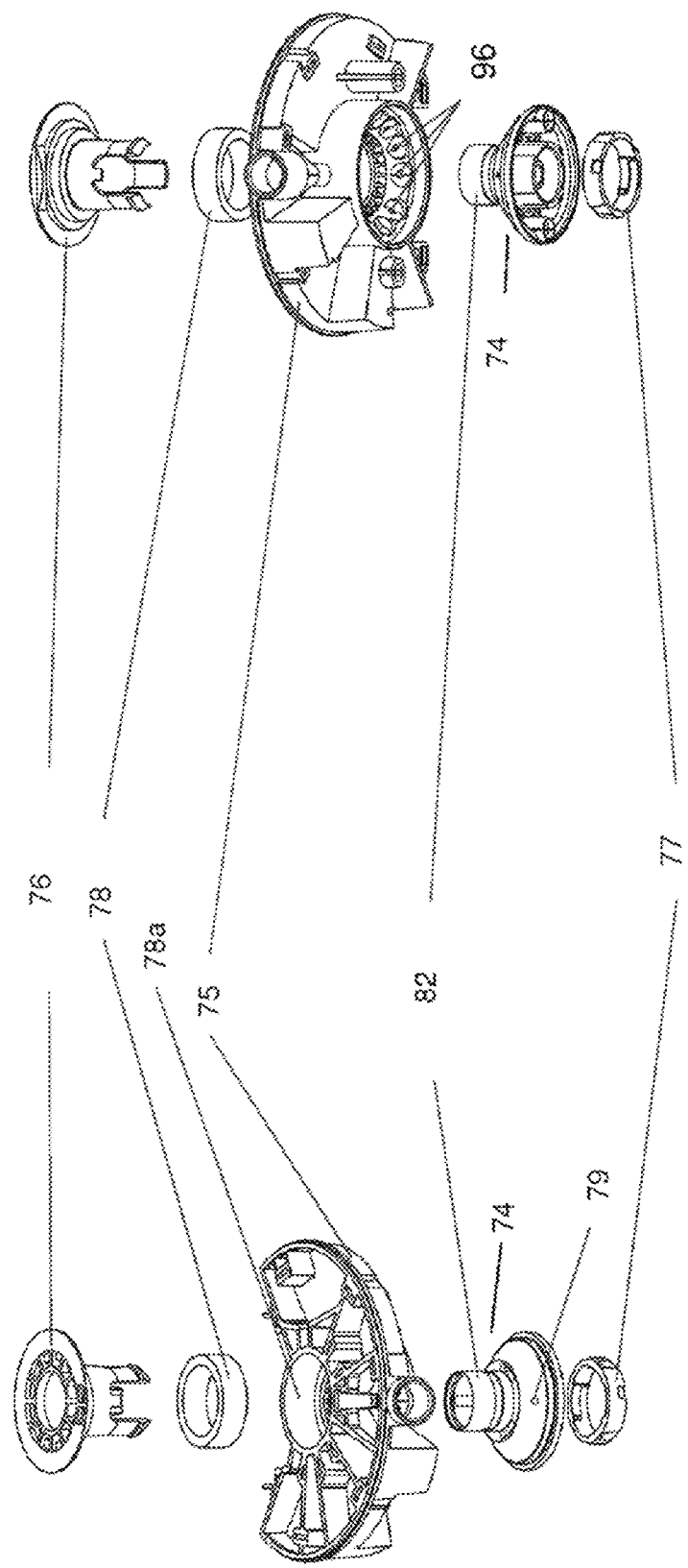
FIG. 4 shows an exploded view of the test cartridge of FIG. 2.

FIG. 3 is a cross-sectional side view of the test cartridge 70 along line A-A, and FIG. 4 shows an exploded view of the test cartridge 70 from above (left) and below (right). A rotating chamber 74 sits generally within the multi-chamber unit 75 and allows transfer of fluid between the chambers. As shown in FIG. 4, the rotating chamber 74 comprises a cylindrical member 82 defining the flow through chamber. When the test cartridge 70 is docked with the base unit 65, the multi-chamber unit 75 cannot rotate, whilst the rotating chamber 74 is able to rotate under the control of a rotational stepper motor 68 of the base unit 65. The rotating chamber 74 and multi-chamber unit 75 are secured between an upper wall component 76 and a locking nut 77.

A spring 78 urges the frustoconical surface of the rotating chamber 74 against the opposed inner surface of the multi-chamber unit 75. A main opening 79 is provided in the frustoconical surface of the rotating chamber 78*a* and communicates with the flow through chamber thereof. A number of apertures 96 are formed around the inner surface of the multi-chamber unit 75, aligned with respective chambers. Each of these apertures is provided with an elastomeric O-ring 80 which provides sealing against the frustoconical surface of the rotating chamber. The apertures are configured such that the opening 79 in the frustoconical surface can be selectively aligned with apertures in the multi-chamber unit 75, whilst the O-ring seals prevent leakage from the unaligned apertures of the multi-chamber unit 75. In the illustrated test cartridge 70, the analysis chamber is not present. Rather, the analysis chamber is plugged into the vacant slot immediately prior to use.

Figure 5A:
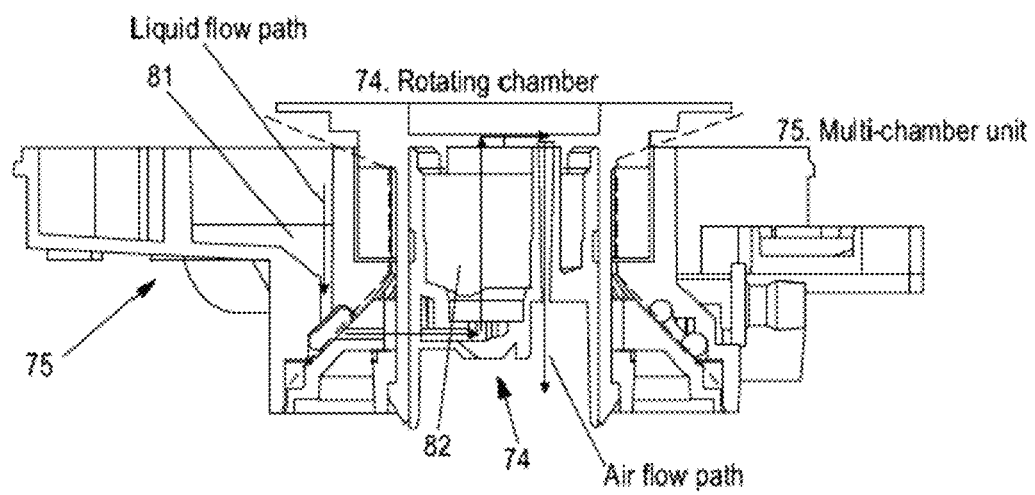
FIG. 5*a* shows the movement of fluid through the test cartridge of FIG. 2.
Figure 5B:
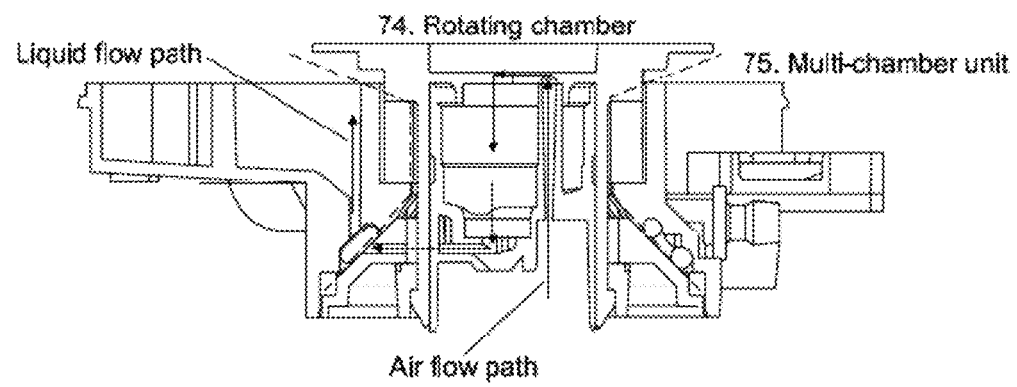
FIG. 5*b* shows the movement of fluid through the test cartridge of FIG. 2

Fluid can be moved between the rotating chamber 74 and chambers of the multi-chamber unit 75 using a syringe (pump) in the base unit to pneumatically move the liquids. This is illustrated in FIGS. 5*a* and 5*b*. FIG. 5*a* illustrates liquid 81 present within one of the chambers of the multi-chamber unit 75, with the aperture of this chamber being aligned with one of the apertures provided in the rotating chamber 74. Air is drawn by the syringe in the base unit through a path indicated by the series of arrows. This path comprises a rotatable coupling between the base unit and the flow through chamber within the cylindrical member 82. This negative pressure causes liquid to be drawn from the chamber of the multi-chamber unit, through the aligned apertures, into the flow through chamber within the cylindrical member 82. FIG. 5*b* illustrates the resulting state, now with a positive pressure being applied to the flow through chamber as indicated by the first set of arrows starting from the right of the Figure. Liquid now begins to flow back from the flow through chamber to the aligned chamber of the multi-chamber unit as indicated by the second set of arrows terminating on the left of the Figure.

When the rotating chamber 74 is filled with liquid, there may be a risk of liquid splashing upwards and then dropping down into the air flow paths connecting to the base unit. The rotating chamber may be provided with a two-way valve, sitting towards the upper end of the cylindrical member 82. This valve allows air to pass under pressure in both directions, i.e., into and out of the chamber, but prevents splashes from moving to the top of the chamber. The valve may be, for example, a "duck-bill umbrella" valve.

Chambers

Referring again to the plan view of the test cartridge shown in FIG. 2, in the present example, four of the nine chambers 95a-i of the upper unit 1 are configured to participate in various stages of a sample analysis procedure in order to perform genotyping or diagnostic testing of a biological sample. The chambers are configured as follows:

Chamber 1/Sample chamber (95a): The input chamber which receives the sample, e.g., by squeezing a drop of the sample from tube 1 through an inlet port (this is described in further detail below).

Chamber 2/Dilution buffer chamber (95b): Contains a dilution buffer to dilute the mixture of lysis buffer and sample in order to lower the pH of the mixture. NB. In the event of a reuse of a cartridge of the type described in WO2018055407, the buffer may be an elution buffer, merely for convenience.

Chamber 3/Mastermix chamber (95c): Contains mastermix beads or solution for preparing the sample for DNA or RNA amplification. The chamber 5c may also comprise desiccant beads.

Chamber 4/Analysis chamber (95d): This chamber contains a chip module which is configured to perform amplification in order to determine the presence of a genetic sequence.

Chamber 5/Waste-Vent chamber (95e): This chamber is empty prior to use and is in liquid communication with a waste sump.

As shown in FIG. 2, the sample chamber 95a comprises an outwards facing port 110 for receiving a drop of lysed sample from the tube 1. The opening is sealed before and after filling by a stopper assembly 111 comprising a stopper and O-ring.

The dilution buffer contained in chamber 95b can be any type of dilution buffer suitable for removing DNA and RNA from the solid phase such as de-ionised water or 10 mM Tris pH 8.5.

The mastermix comprises all of the reagents necessary for performing the chosen method of amplification, apart from the primers and, in the case of PCR, a template. These additional components are provided within the amplification unit 71. When the amplification method is PCR, the mastermix can comprise, for example, Taq DNA Polymerase, dNTPs, $MgCl_2$ a reaction buffer optimised for PCR and a fluorescent compound. A mastermix for LAMP can comprise a DNA polymerase, enzymes and a dye. When the amplification method is RT-PCR or RT-LAMP, the mastermix will also comprise a reverse transcriptase.

The above arrangement of chambers is only one possible arrangement that is suitable for analysing a sample comprising genetic material. In the present example, some of the chambers of the test cartridge 70 are redundant. Of course, other arrangements are envisaged in which more, or fewer, of the chambers are used in the workflow, and wherein different reagents are stored in any combination of the chambers partaking in the workflow.

Base Unit

Figure 6:
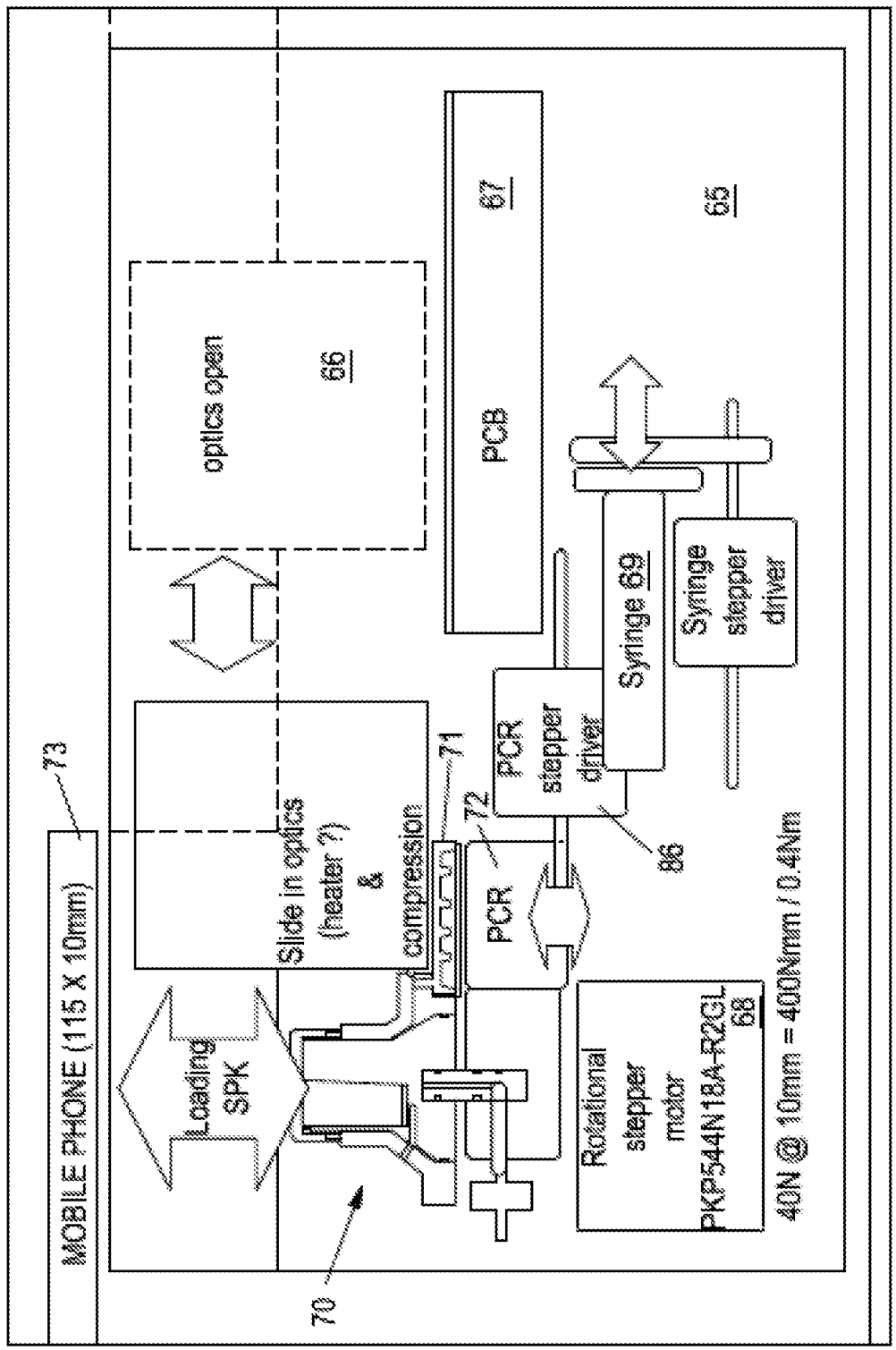
FIG. 6 illustrates schematically a base unit for operating the test cartridge of FIG. 2.

The movement of fluid between the chambers of the test cartridge 70 is controlled by base unit 65, illustrated schematically in FIG. 6. The base unit 65 comprises a number of components including optics 66, a PCB 67, a rotational stepper motor 68, and a syringe 69. In this system, the optics 66 can be slid to the right (as viewed in the Figure) to allow a test cartridge 70 (only part of which is shown in the Figure) to be inserted into the base unit from above. Once inserted, the optics are slid to the left so that they sit above the analysis unit 71 of the test cartridge. The system is then initialised, causing a PCR stepper driver to press a Peltier module 72 (used to perform the amplification step) upwards against an under surface of the analysis unit 71. As the optics cannot move in the vertical direction, the analysis chamber is squeezed between the Peltier module and the optics, forcing liquid into the wells of the analysis unit 71.

Analysis Unit

The analysis unit 71 installed in the analysis chamber 95b comprises a chassis containing a plate having a plurality of wells comprising spotting reagents for performing amplification and detection of DNA or RNA. The analysis unit may be configured to perform PCR or LAMP amplification. Visible results are produced from the amplification step to confirm the presence of specific sequences of DNA or RNA.

Figure 7:
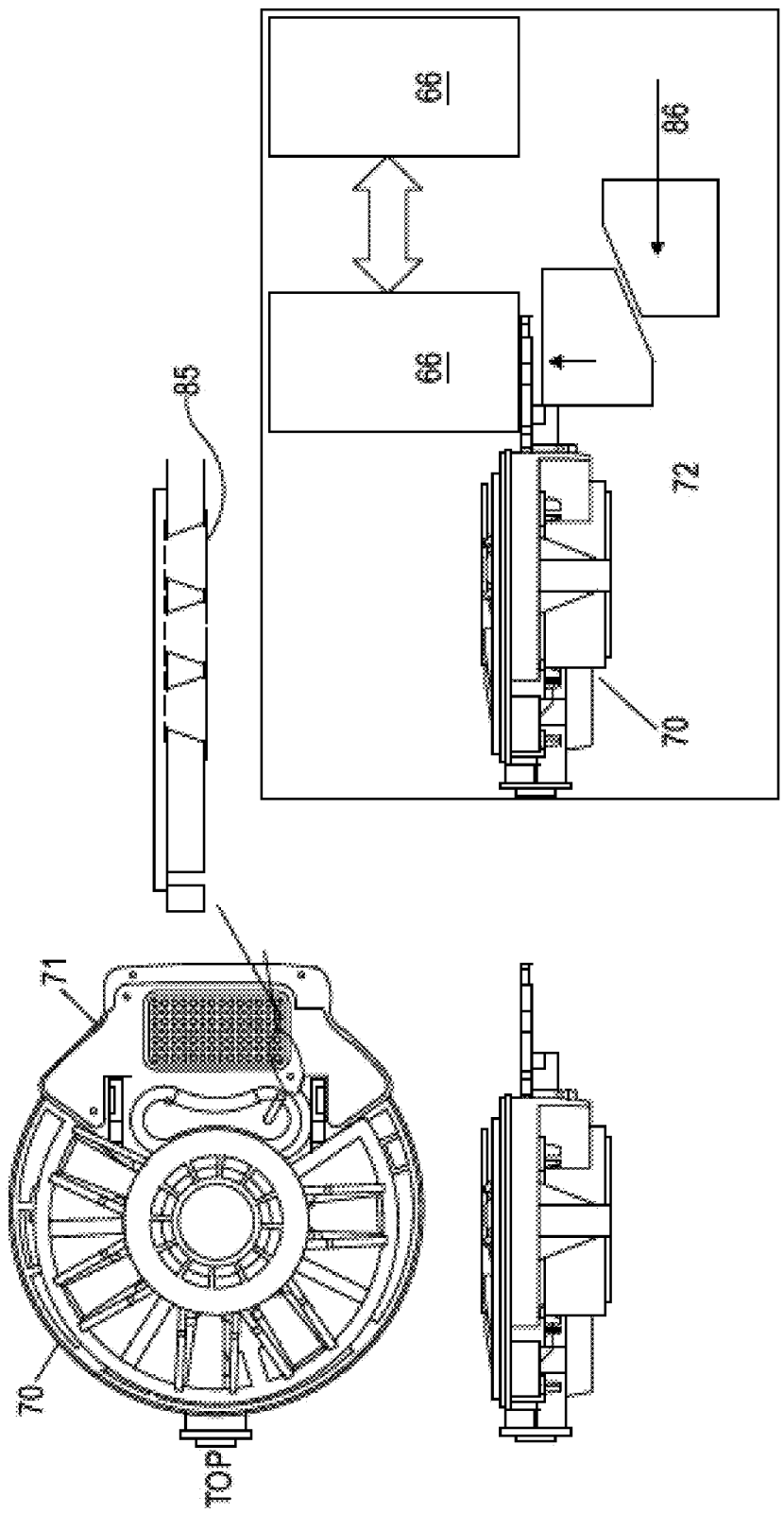
FIG. 7 is a plan view of the test cartridge of FIG. 2, including an analysis unit.

FIG. 7 further illustrates, in various views, the test cartridge 70 with the analysis unit 71 installed. The analysis chamber 71 comprises an array of wells 84 within which the amplification reaction occurs and within which the visible results are produced. In the absence of a sufficiently high liquid injection pressure, it is not generally sufficient to fill the wells by merely flowing liquid across the surface. Rather, a pressure needs to be applied in order to squeeze liquid into the wells. To achieve this, the base 85 of the wells is formed by a material that allows air to pass through, but which is impermeable to liquid. Once the test cartridge 70 has been installed into the base unit, the optics 66 slid into place, and liquid transported in the analysis unit 71 so as to cover the array of wells, a linear actuator 86 is engaged with the Peltier module 72 in order to bias the bottom of the analysis chamber upwards, pressing the top of the analysis chamber against the bottom of the optics. This exerts a pressure on the liquid above the wells, forcing it into the wells in order to achieve satisfactory fill levels. This clamping pressure also ensures good thermal contact between the base of the analysis unit 71 and the Peltier module 72.

Figure 8:
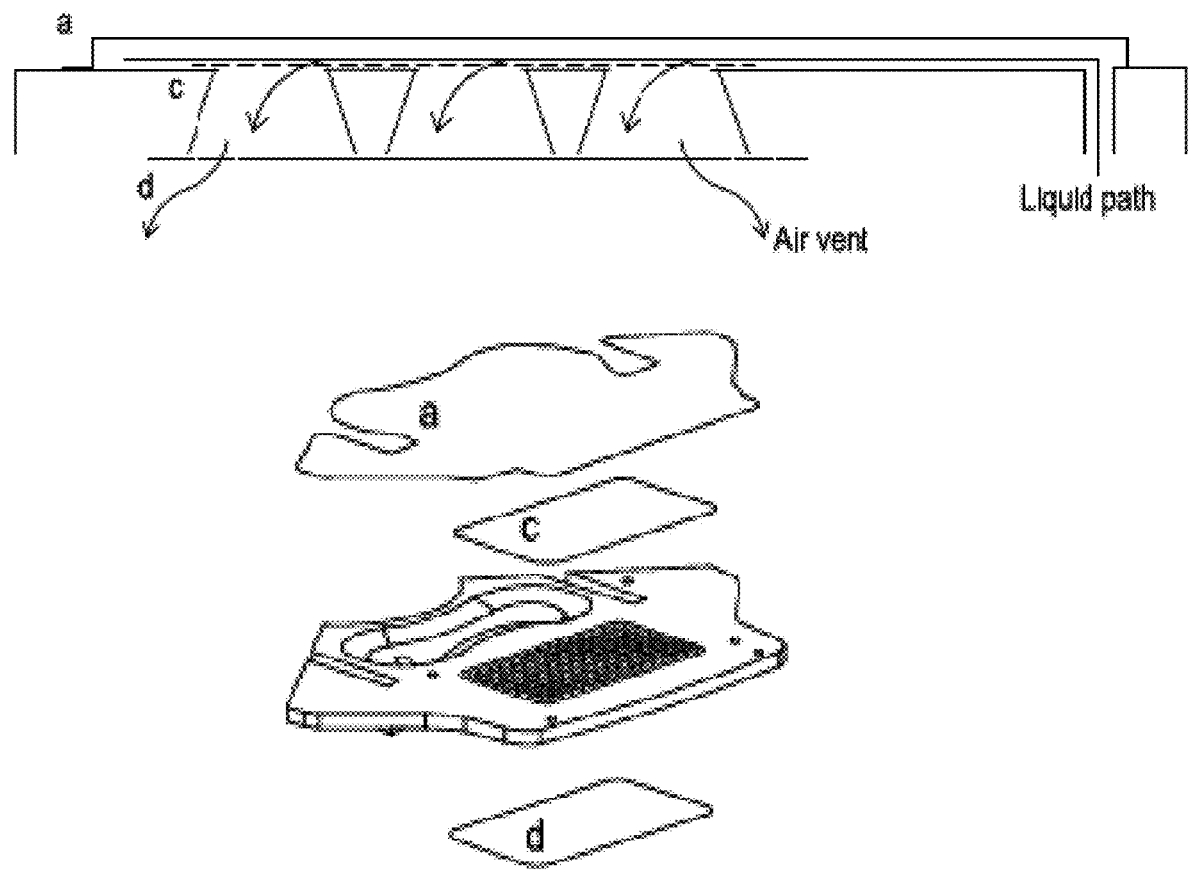
FIG. 8 shows the analysis unit of the test cartridge of FIG. 2 in more detail.

This mechanism for applying pressure above the wells to fill the wells is further illustrated in FIG. 8. As well as a liquid and air impermeable membrane (a) above the wells and a liquid impermeable and air permeable (hydrophobic) layer (d) below the wells, an air and liquid permeable layer (c) is fixed directly on top of the wells beneath the layer (a) and is sealed to the surface between the wells. The purpose of this layer (c) is two-fold. Firstly, it provides resistance to well filling so that the wells do not fill while the volume between layers (a) and (c) is being filled. This minimises the risk of material being carried between wells during filling. Secondly, once the wells are filled the layer (c) can provide some resistance to "cross-talk" between wells. Layer (c) may be relatively hydrophobic with a mesh size sufficient to prevent the passage of liquid unless the liquid pressure exceeds some required level. Cross-talk is also reduced due to the clamping of the layer (a) against the surface by the optics. In some cases layer (c) may be omitted. As will be apparent to the skilled person, one or more biomarkers (e.g., primers/probes) will be provided within the well, or made available to the well, in order to perform the analysis. In one embodiment, the biomarker(s) may be spotted or otherwise fixed to the upper surface the hydrophobic layer (d).

Piercing Arms

Figure 9:
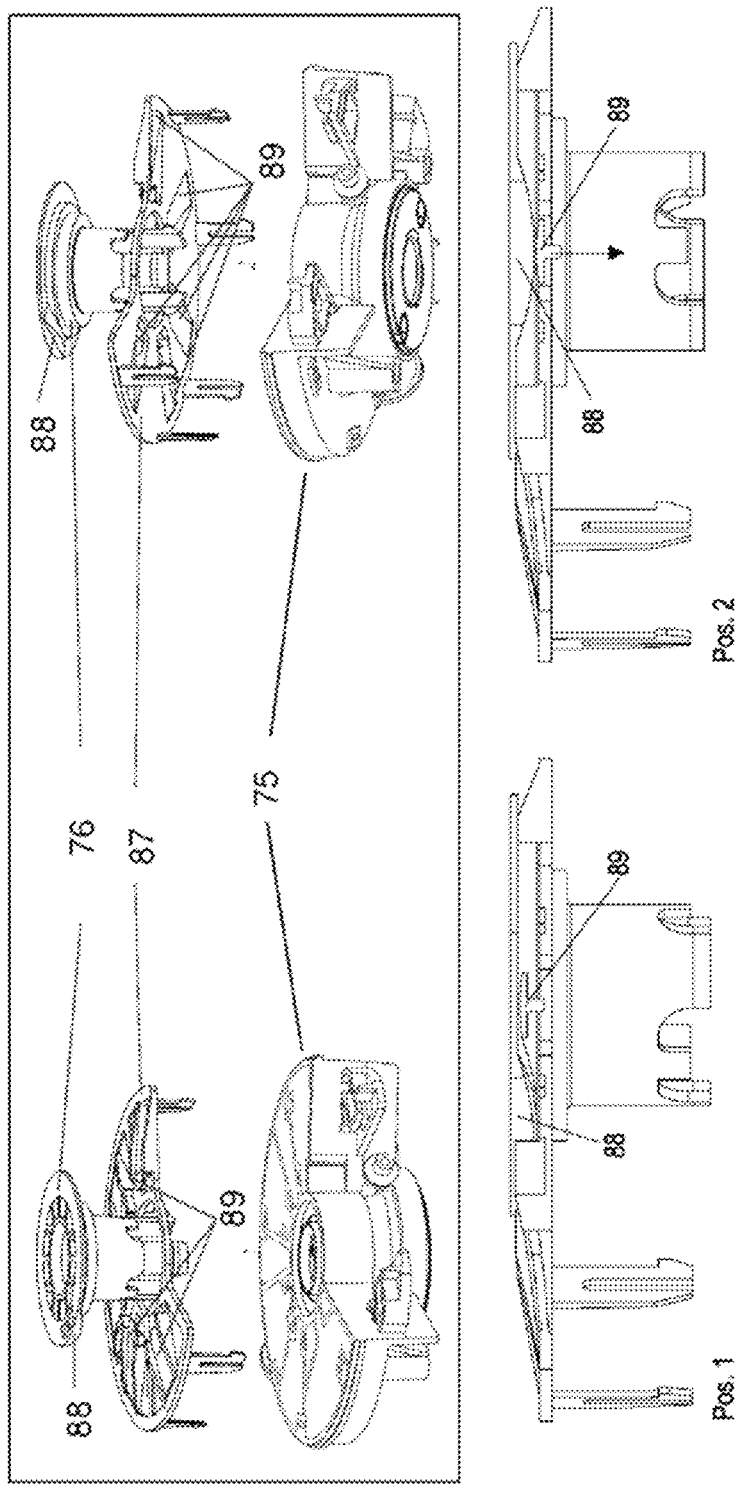
FIG. 9 shows a piercing component of the test cartridge of FIG. 2.

In some cases, it may be necessary to provide air flow channels into each of the chambers of the multi-chamber unit in order to allow liquid to flow in and out of the chambers. However, it is preferable that such channels are formed only at the time of use to avoid contamination. FIG. 9 illustrates one possible mechanism for achieving this and relies upon the provision of a foil or other breakable component on top of some of the chambers that will be used in the workflow. In the present example, the sample chamber 95*a*, the elution chamber 95*b*, and the mastermix chamber 95*c* will comprise foil coverings. An intermediate component 87 is located above the multi-chamber unit 75 and has a small degree of movement in an axial direction relative to multi-chamber unit. However, the component 87 and the multi-chamber unit 5 cannot rotate relative to one another. The upper wall component 76 is modified to include one or more cams 88 which are able to exert a downward force onto the intermediate component 87. When the test cartridge 70 is installed into the base unit 65 and the rotating chamber first rotated together with the upper wall component 76, the cams 88 act to press the component 87 down onto the multi-chamber unit 75. This in turn causes a set of piercing arms 89, aligned with respective chambers, to pierce the foil covers on the chambers thereby venting the chambers to the surrounding environment. Whilst the piercing arms 89 may be raised subsequently as the rotating chamber is further rotated, the venting paths remain open.

The multi chamber unit 75 and intermediate component 87 are constructed of a suitable polymer such as Polypropylene, PTFE or COC. Advantageously, the intermediate component 87 may be made of a transparent polymer to allow a user to view certain steps in the analysis process. A barcode may be located on the outer surface of the top cover so the test cartridge 70 can be identified.

Method

In one embodiment, illustrated in FIG. 7, a workflow for analysing a biological sample using the kit of FIG. 1 and the test cartridge 70 of FIG. 2 is as follows, assuming the use of the swab 2 to collect a biological sample comprising genetic material:

Lyse—The head of the swab 2, which contains a biological sample (e.g., following a cheek swabbing action), is introduced in the tube 1 containing lysis buffer. The head of the swab 2 is thoroughly agitated in the lysis buffer by moving the head of the swab up and down, sidewise etc, for about 10 s. Once the swab 2 has been removed from the tube 1, the open end of the tube 1 is closed with the cap 5.

Optionally, aluminium oxide powder may be added to the mixture of the biological sample and lysis buffer in the tube 1 in order to promote lysis and inactivate nucleases. This acts to increase the concentration of genetic material in the mixture.

Figure 10:
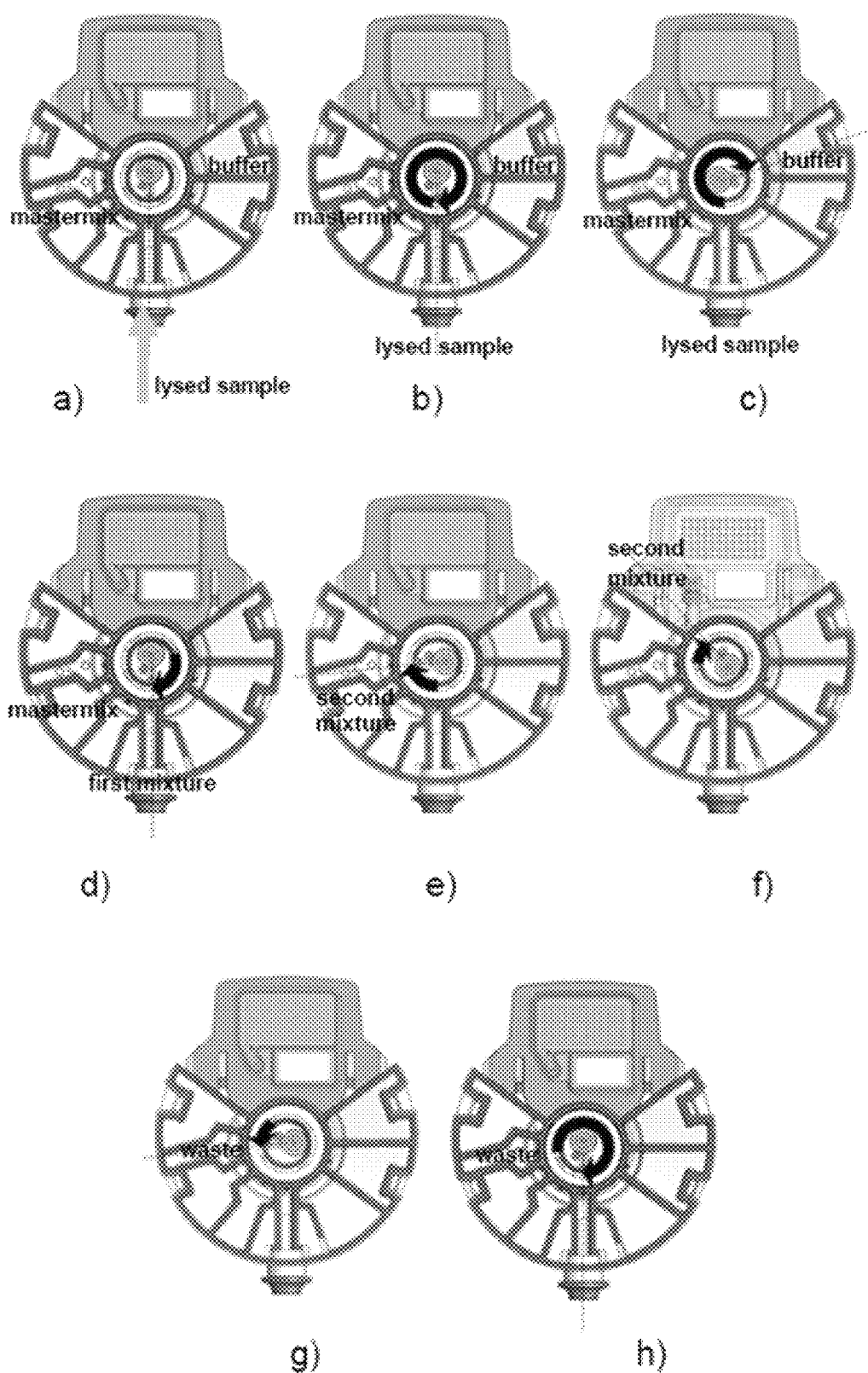
FIG. 10 shows a number of stages in the processing of a sample using the test cartridge of FIG. 2.

Input—The stopper of the sample chamber 95*a* is removed and the tube 1 is squeezed to push one drop of the lysed sample through the cap 5 of the tube 1 and into the sample chamber through the inlet port 110. The stopper of the sample chamber 95*a* is then replaced. FIG. 10*a*.

Pierce—The rotating chamber 74 is rotated to align the opening 79 of the rotating chamber 74 with the opening 96 of the sample chamber 95*a*. The rotating chamber is then rotated 360 degrees to operate the piercing arms to pierce the foil covering the sample chamber 95*a*, the elution buffer chamber 95*b* and the mastermix chamber 95*c* to provide air vents in the foil covers of the respective chambers. FIG. 10*b*.

Elute—The rotating chamber 74 is rotated to align the opening 79 of the rotating chamber 74 with the opening 96 of the dilution buffer chamber 95*b*. A negative pressure is generated in the rotating chamber 74 to displace the dilution buffer from the dilution buffer chamber 95*b* to the rotating chamber 74. The rotating chamber 74 is then rotated to align the opening 79 of the rotating chamber 74 with the opening 96 of the sample chamber 95*a*. A positive pressure is generated in the rotating chamber 74 to displace the dilution buffer from the rotating chamber 74 to the sample chamber 95*a* to obtain a first mixture of lysed sample and dilution buffer. FIGS. 10*c* and 10*d*.

Mastermix—A negative pressure is generated in the rotating chamber 74 to displace the first mixture from the sample chamber 95*a* to the rotating chamber 74. The rotating chamber 74 is then rotated to align the opening 79 of the rotating chamber with the opening 96 of the mastermix chamber. A positive pressure is then generated in the rotating chamber 74 to displace the first mixture from the rotating chamber 74 to the mastermix chamber 95*c*. A second mixture is obtained of the first mixture and mastermix. FIG. 10*e*.

Amplify—A negative pressure is generated in the rotating chamber 74 to displace the second mixture from the mastermix chamber 95*c* to the rotating chamber 74. The rotating chamber 74 is then rotated to align the opening of the rotating chamber 74 with the opening 96 of the analysis chamber 95*d*. A positive pressure is then generated in the rotating chamber 74 to displace the second mixture from the rotating chamber 74 to the analysis chamber 95*d*. The genetic material present in the second mixture reaching the analysis unit installed in the analysis chamber is amplified by a PCR or LAMP procedure to perform genotyping or diagnostic testing. FIG. 10*f*.

Waste disposal—A negative pressure is generated in the rotating chamber 74 to displace the remains of the second mixture, i.e., waste material that was not received by the analysis unit, from the analysis chamber to rotating chamber 74. The rotating chamber is then rotated to align the opening 79 of the rotating chamber with the opening 96 of the mastermix chamber. A positive pressure is generated in the rotating chamber 74 to displace waste material from the rotating chamber 74 to the mastermix chamber. FIG. 10*g*.

Finish—The rotating chamber 74 is rotated to align the opening 96 of the rotating chamber 74 with the opening 96 of the sample chamber to signal the end of the workflow. FIG. 10*h*.

Figure 11:
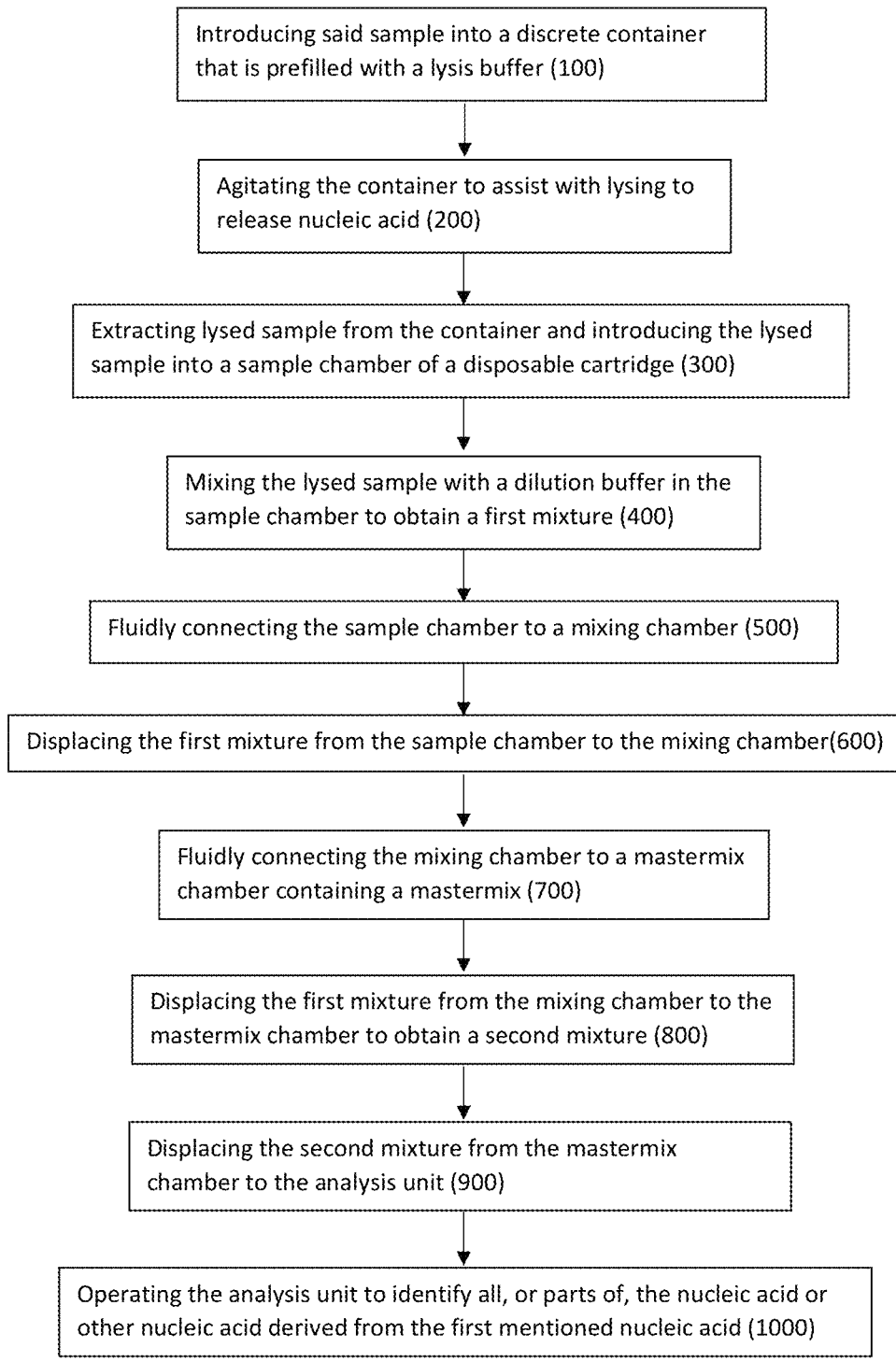
FIG. 11 is a flow diagram illustrating steps for analysing a biological sample.

FIG. 11 is a flow diagram further illustrating steps involved in identifying all, or parts of, the nucleic acid (or other nucleic acid derived from the first mentioned nucleic acid) and which may be a precursor to genotyping or diagnosis.

Advantageously, by lysing the biological sample in a high pH buffer, cell lysis can take place in a matter of seconds. Further, by performing the lysis step outside of the test cartridge 70, fewer processing steps have to be conducted using the cartridge itself, which makes the cartridge workflow less time consuming. Since the lysis step can be easily performed by a consumer or subject, this step can be performed first and then presented to an operator of the test cartridge. It is noted that the lysis buffer is relatively non-toxic as far as the required reactions are concerned and therefore a washing step is unnecessary. In particular, the use of the toxic buffer guanidine hydrochloride is avoided.

In addition, and surprisingly, as compared to the procedure described in WO2018055407, the entire contents of which are hereby incorporated by reference in its entirety, it has been found that the use of a frit to extract DNA from the lysed sample and hold it for washing is unnecessary. Rather, the lysed sample can be mixed first with the dilution buffer in the sample chamber, and the resulting combined sample transferred directly to a chamber containing the mastermix, before introducing the resulting mixture to the analysis chamber. The number of liquid transfer stages is significantly reduced. As each transfer stage can involve multiple operations of the syringe in the base unit to force air into and out of the mixing chamber, this represents a significant time saving. This in turn allows for more rapid genotyping and diagnostic testing and reduces the cross-infection risks. Indeed, as compared to the procedure described in WO2018055407, the sample preparation time, i.e., the time to provide the prepared sample to the AU once the lysed sample is introduced to the sample chamber, may be reduced from around 15 minutes to round 1.5 minutes.

Although the processing steps before amplification could be considered a "crude" way to extract genetic material, the amounts of genetic material extracted by this method are sufficient to perform the amplification of the strands of DNA or RNA necessary for performing limited identification of a nucleic acid sequence or parts of such a sequence and, optionally, any SNP genotyping or diagnostic testing. The methods employed herein are thus sufficient for genotyping of specific SNPs, or for identifying genetic fragments specific for confirming the presence of certain pathogens in the biological sample.

Although the cartridge described herein comprises a central rotating chamber 74 surrounded by multiple chamber 95a-i, other designs are envisaged in which fewer chambers are used to prepare the sample for analysis.

What is claimed is:

1. A method of analysing a sample comprising nucleic acid, the method comprising:
   introducing said sample into a discrete container that is prefilled with a lysis buffer;
   agitating the container to assist with lysing to release nucleic acid;
   extracting lysed sample from the container and introducing the lysed sample into a sample chamber of a disposable cartridge;
   mixing the lysed sample with a dilution buffer in the sample chamber to obtain a first mixture of lysed sample and dilution buffer;
   fluidly connecting the sample chamber to a mixing chamber of the disposable cartridge;
   displacing the first mixture from the sample chamber to the mixing chamber;
   fluidly connecting the mixing chamber to a mastermix chamber of the disposable cartridge containing a mastermix;
   displacing the first mixture from the mixing chamber to the mastermix chamber to obtain a second mixture;
   displacing the second mixture from the mastermix chamber to an analysis unit; and
   operating the analysis unit to identify all, or parts of, the nucleic acid or other nucleic acid derived from the first mentioned nucleic acid.

2. A method according to claim 1, where said sample contains biological cells containing said nucleic acid.

3. A method according to claim 1, where said nucleic acid is DNA or RNA.

4. A method according to claim 1, wherein the sample is lysed in lysis buffer with a pH between 12 and 14.

5. A method according to claim 1, wherein the step of operating the analysis unit comprises operating the analysis unit to identify all, or parts of, the nucleic acid or other nucleic acid using PCR or LAMP.

6. A method according to claim 1, wherein said step displacing the second mixture from the mastermix chamber to the analysis unit comprises:
   displacing the second mixture from the mastermix chamber back into the mixing chamber;
   fluidly connecting the mixing chamber to an analysis unit; and
   displacing the second mixture from the mixing chamber to the analysis unit.

7. A method according to claim 6, wherein displacement of mixtures between the various chambers is achieved by applying a positive or negative air pressure to the mixing chamber.

8. A method according to claim 1, wherein said sample chamber and said mastermix chamber are provided within an outer housing of a disposable cartridge, and said mixing chamber is provided within an inner housing of the disposable cartridge, the inner and outer housings being rotatable relative to one another about a central axis in order to facilitate said steps of fluidly connecting.

9. A method according to claim 1, the steps being performed in sequence and without any intervening elution and/or washing steps.

10. A method according to claim 1, wherein said step of agitating the container comprises manually agitating the container.

11. A method according to claim 1, wherein the analysis unit is installed in the disposable cartridge.

* * * * *